United States Patent [19]

Graber

[11] Patent Number: 4,823,841

[45] Date of Patent: Apr. 25, 1989

[54] FLUID MIXING DEVICE, IN PARTICULAR HOT AND COLD WATER MIXING DEVICE

[75] Inventor: Heinz Graber, Oberkulm, Switzerland

[73] Assignee: KWC AG, Unterkulm, Switzerland

[21] Appl. No.: 246,750

[22] Filed: Sep. 20, 1988

[30] Foreign Application Priority Data

Oct. 1, 1987 [CH] Switzerland ............ 3827/87

[51] Int. Cl.[4] .................. F16K 21/04; F16K 3/02; F16K 11/18
[52] U.S. Cl. .................. 137/625.41; 137/614.16; 137/614.17; 251/64
[58] Field of Search ............ 137/614.16, 614.17, 137/614.18, 625.41; 251/64

[56] References Cited

U.S. PATENT DOCUMENTS 4,178,963 12/1979 Riefler et al. .............. 137/625.41 X
4,624,281 11/1986 Vidal et al. ............... 137/614.17 X

FOREIGN PATENT DOCUMENTS 650309 9/1937 Fed. Rep. of Germany ............... 137/614.16
651119 8/1985 Switzerland .
654088 1/1986 Switzerland .

*Primary Examiner*—Arnold Rosenthal
*Attorney, Agent, or Firm*—Werner W. Kleeman

[57] ABSTRACT

The hot and cold water mixing device contains a rotary slide which controls in opposite sense the inflow of cold and hot water. The rotary slide is provided with a device for suppressing the flow of hot and cold water through the rotary slide. In order to render the mixing valve smooth in operation and to simplify its construction, without eliminating the advantages of such construction of mixing device, the flow suppressing device is formed by a closure portion or element of a servo valve, and the rotary slide is structured to serve as a seat for such closure portion or element.

13 Claims, 2 Drawing Sheets

FLUID MIXING DEVICE, IN PARTICULAR HOT AND COLD WATER MIXING DEVICE

BACKGROUND OF THE INVENTION

The present invention broadly relates to fluid mixing devices, and, in particular, concerns a new and improved construction of a hot and cold water mixing device, sometimes also referred to in the art as a mixing battery, plumbing mixing fixture or mixing tap. In the description to follow the fluid mixing arrangement of this invention will generally simply be referred to as a mixing device.

Generally speaking, the mixing device of the present development is of the type comprising a rotary slide or slide member which controls in an opposing sense or inversely the inflow of the hot and cold water. This mixing device is provided with a device or means in order to suppress or prevent the flow of water through the rotary slide or slide member.

Prior art constructions of mixing devices or mixing batteries of the aforementioned type, specially so-called single lever-mixing devices or mixing batteries, for instance as disclosed in Swiss Pat. No. 651,119, granted Aug. 30, 1985 or Swiss Pat. No. 654,088, granted Jan. 31, 1986, are designed such that it is possible to place the mixing device in a closed position or state by accomplishing a translatory displacement of the rotary slide with respect to the inlets and/or the outlet of the mixing valve. Due to such translatory displacement of the rotary slide, the openings or ports in the rotary slide no longer flow communicate or register with the inlets or the outlet, as the case may be. This construction, wherein the rotary slide has the form of a disk or plate, preferably formed of a hard material such as ceramic, which sealingly bears at a counter disk having two inlet openings and one outlet opening, has proven itself in practice, above all because the rotary slide cannot be overloaded in its closed position. However, it is to be observed that this advantageous construction is achieved at the expense of a relatively complicated and cumbersome structural design.

First of all, the rotary slide, independent of its position, always must cleanly sealingly bear at the counter disk. That result only then can be achieved if the rotary slide is very accurately machined so as to be quite flat or planar and if it is always pressed with a certain contact or pressing force against the counter disk. It is for these reasons that such construction is also construed to be relatively cumbersome or complicated. Additionally, the single operating lever must be rotatable or pivotable about two pivot axes which are disposed or postured approximately at right angles to one another. The rotation of the operating lever about the axis of the mixing device or mixing battery generally determines the relative rotational position of the rotary slide in relation to the inlets leading to the mixing device and thus the mixing ratio of the mixed hot and cold water which effluxes from the outlet. On the other hand, the degree of pivoting of the operating lever about the pivot axis disposed perpendicular to the axis of the mixing device governs the throughflow quantity, that is to say, the degree of opening of the hot and cold water mixing device.

It is to be recognized that there exist numerous fields of application where there is not required at all regulation of the throughflow quantity of the hot and cold water. Quite to the contrary, what is required is only the regulatability of the mixing ratio of the hot and cold water and easy operability of the mixing device, in other words it should be user-friendly

SUMMARY OF THE INVENTION

Therefore with the foregoing in mind it is a primary object of the present invention to provide a new and improved construction of a fluid mixing device, especially a hot and cold water mixing device, which is not afflicted with the aforementioned shortcomings.

Another and more specific object of the present invention aims at the provision of a new and improved construction of a mixing device of the previously mentioned type which, while retaining the advantages of the heretofore known prior art constructions of mixing devices, in particular the advantageous feature that there is not overloaded the rotary slide in its closed position, can be operated in an extremely easy or facile manner and which in any event so-to-speak "gently" or smoothly opens and above all closes, so that pressure peaks can be beneficially avoided in the infeed lines or conduits for the hot and cold water.

Yet a further notable object of the present invention is directed to an improved construction of a hot and cold water mixing device or mixing battery, which is relatively simple in construction and design, quite economical to manufacture, extremely reliable in operation, not readily subject to breakdown or malfunction, and requires a minimum of maintenance and servicing.

Now in order to implement these and still further objects of the invention, which will become more readily apparent as the description proceeds, the fluid mixing device for hot and cold water as contemplated by the present invention, among other things, is manifested by the features that the means or device for suppressing the throughflow of the hot and cold water by the action of the rotary slide or slide member is constituted by a closure portion or element of a servo valve, and that the rotary slide is structured as a seat for the closure portion or element.

By using a servo valve, it is the pressure, which is usually a constant pressure, prevailing in the infeed lines or conduits leading to the mixing device or battery, which governs the closing force of the closure portion or element against the rotary slide or slide member which is constructed as a seat for such closure portion or element. Additionally, the use of a servo valve, by virtue of the inherent characteristics or properties thereof, namely the comparatively haling opening and closing action, which in any event avoids pressure peaks in the infeed lines or conduits.

BRIEF DESCRIPTION OF THE DRAWINGS

The invention will be better understood and objects other than those set forth above will become apparent when consideration is given to the following detailed description thereof. Such description makes reference to the annexed drawings wherein throughout the various figures of the drawings, there have been generally used the same reference characters to denote the same or analogous components and wherein.

DETAILED DESCRIPTION OF THE PREFERRED EMBODIMENTS

Figure 2:
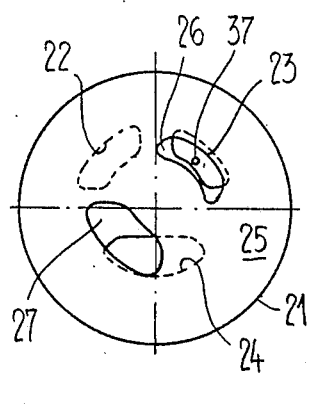
FIGS. 2, 3 and 4 respectively depict in top plan view, looking in the direction of the plane or section line A—A of FIG. 1 upon the rotary slide or slide member and the counter disk or plate located therebelow, different rotational positions of such rotary slide or slide member.
Figure 3:
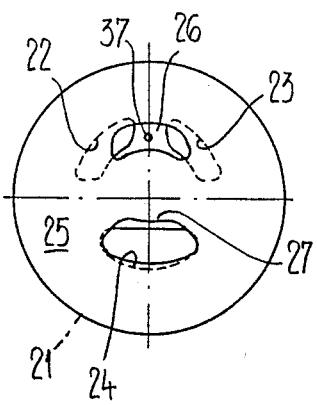
Figure 4:
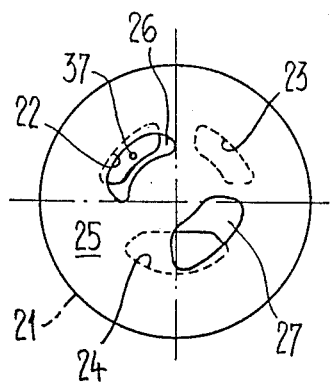

Describing now the drawings, it is to be understood that in order to simplify the illustration thereof, only enough of the construction of the exemplary embodiment of fluid mixing device or battery, here the hot and cold water mixing device has been depicted as needed for those skilled in the art to readily understand the underlying principles and concepts of the invention. Turning attention now specifically to FIG. 1, the therein illustrated exemplary embodiment of mixing device or mixing battery 10 for hot and cold water will be seen to comprise a connection arrangement or connecting socket 11 or equivalent structure in which there are formed two inlets or intakes 12 and 13, for cold and hot water, as well as an outlet or outtake 14 for the mixed water. The inlets 12 and 13 are arranged behind one another in the plane of the drawing of FIG. 1. Seated in the connection arrangement 11 is a substantially cup-shaped cartridge or insert member 15. The floor or bottom portion or base 15a of this substantially cup-shaped cartridge or insert member 15 possesses throughpassages or openings 16, 17 and 18 which flow communicate with the inlets 12, 13 and the outlet 14, respectively. These throughpassages or openings 16, 17 and 18 are mutually sealed with respect to one another and with respect to the connection arrangement 11 by seals or sealing means 19. A counter disk or plate member 21 is located internally of the substantially cup-shaped cartridge or insert member 15 and sealingly bears by means of the seals or seal means 20 against the floor or base 15a of such cartridge or insert member 15. As will be seen by also inspecting FIGS. 2 to 4, this counter disk or plate member 21 possesses two inlet openings or apertures 22 and 23 as well as an outlet opening or aperture 24. The counter disk 21, preferably formed of a hard material, for instance ceramic, is seated so as to be non-rotatable within the substantially cup-shaped cartridge or insert member 15 and coacts with a substantially disk-shaped rotary or displaceable slide or slide member 25 which possesses an inlet-side throughpassage or opening 26 and an outlet-side throughpassage or opening 27.

At the side 25a of the rotary slide 25, and which side faces away from the counter disc or plate member 21, there sealingly bears an entrainment or drive bell or hood member 28. The lower edge or edge region 28a of this entrainment bell or hood member 28 is provided with protruberances or projections 29 or equivalent structure which engage in complementary notches or recesses 30 or the like provided at the circumferential region of the rotary slide or slide member 25. The entrainment bell or hood member 28 which is thus rigidly or positively connected for rotation with the rotary slide 25, delimits or bounds a first chamber or compartment 31 in which there is arranged a closure portion or element 32 of a servo valve 100 as will be explained more full hereinafter. The seat of this closure portion or element 32 is formed by the side or face 25a of the rotary slide 25 which faces away from the counter disk or plate member 21.

This closure portion or element, 32 comprises a valve plate or plate member 33 in which there is mounted a seal or seal member 34 which covers the throughpassages or openings 26 and 27 provided in the rotary slide or slide member 25. The closure portion or element 32 defines a membrane or diaphragm structure.

The valve plate 33 is formed of one-piece or integrally with an essentially cylindrical shaft or shaft member 35 which, in turn is mounted to be lengthwise displaceable, however non-rotatable in a bore 36a of a prolongation or extension 36 which is formed at the entrainment bell or hood member 28.

At the region of the inlet-side throughpassage 26 the seal or seal member 34 and the valve plate 33 are pierced by a first throttle opening 37 extending therethrough. By means of this throttle opening 37 one or the other or both inlet openings 22 and 23 are continuously connected in flow communicating fashion with the first chamber 31. In this regard attention is also directed to FIGS. 2 to 4 in which there has been shown a reference position of the first throttle opening 37 relative to the inlet-side throughpassage 26.

The shaft 35 is provided with a blindhole bore 38 which opens into a further chamber or compartment 39 which is formed in an entrainment or coupling sleeve or sleeve member 40. This entrainment sleeve or sleeve member 40 engages by means of claw-like projections or dogs 41 or equivalent structure into gaps or spaces which are formed between projections or protrusions 42 of the entrainment bell or hood member 28. These protrusions or projections 42 or the like laterally protrude from the prolongation or extension 36. In this way the entrainment or coupling sleeve 40 and the entrainment bell or hood member 28 are rigidly coupled for rotation with one another, in other words are rigidly connected so as to be non-rotatable in relation to one another.

The entrainment or coupling sleeve or sleeve member 40 is axially held down or depressed via a slide ring seal 43 by an inwardly protruding shoulder 44 of a threaded ring or ring member 45. This threaded ring or ring member 45 is threadably connected to the upper end 11a of the connection arrangement 11. The holddown force which is effective upon the entrainment sleeve 40 is transmitted by a spacer or distancing element 46 also to the entrainment bell or hood member 28.

A second throttle opening 47 extends from the chamber or compartment 31 and pierces through the base or foot region 35a of the shaft or shaft member 35. This second throttle opening 47 flow communicates with the blindhole or blindhole bore 38. An annular or ring-shaped chamber or space 48 is provided between the entrainment sleeve 40 and the entrainment bell or hood member 28. This annular or ring-shaped chamber or space 48 flow communicates with the outlet-side throughpassage or opening 27 by means of channels 49 and 50 which are provided in the spacer element 46 and in the rotary slide or slide member 25.

Continuing, it will be observed that the chamber 39 and the annular or ring-shaped chamber 48 are in flow communication with one another by a pilot valve 51 or equivalent valve structure which is pre-biased in the valve closing direction. This pilot valve 51 comprises a valve closure portion 52 secured to a plunger or stem member 53. This plunger 53 is displaceably mounted in a lateral bore 40a provided in the entrainment or coupling sleeve 40.

The entrainment or coupling sleeve 40 possesses a head portion or headpiece 54 which is pierced or through which extends a central threaded bore or hole 55 having a single-or multiple-thread internal threading or thread structure 55a possessing a very large thread pitch. A threaded pin or pin member 56 provided with appropriate external threading or thread means, generally indicated by reference character 56a, engages into the threaded bore or hole 55. This threaded pin 56 is mounted to be rotatable, however axially non-displaceable in a central bore 57a of a bowl or dish portion 57 which, in turn, is fixedly clamped in a suitable hand grip 58a, here shown as an operating or manipulating cap or cap member 58, by means of a threaded ring or ring member 59 which is threaded into this operating or manipulating cap 58. The bowl or dish portion 57 is supported, on the one hand, at the head portion 54 of the entrainment or coupling sleeve 40 by means of a compression or pressure spring 60 defining return spring means and, on the other hand, is rigidly connected for non-relative rotation with the entrainment sleeve 40 by means of claw-like teeth 60' which engage with notches or recesses 61 or the like formed at the head portion 54.

The operating cap or cap member 58 and the bowl or dish portion 57 delimit or confine a chamber 62 in which there can be housed a here only schematically depicted mechanism 63 which can be actuated by the threaded pin or pin member 56 and the function of which mechanism 63 will be considered more fully hereinafter.

To ensure that the operating or manipulating cap 58 is not undesirably or unduly raised or lifted in conjunction with the bowl or dish portion 57 by the action of the compression or pressure spring 60 this operating or manipulating cap 58 is secured by a laterally screwed-in threaded pin or pin member 63' which engages in a circumferential or peripheral groove 64 which is formed at the outside or outer surface of the threaded ring or ring member 45. This circumferential groove 64 has a sufficient height or depth to ensure that the operating or engagement cap 58 and the parts of components which are fixedly clamped thereat can be depressed or pushed-in through a predeterminate distance or extent against the action of the compression or pressure spring 60.

Figure 1:
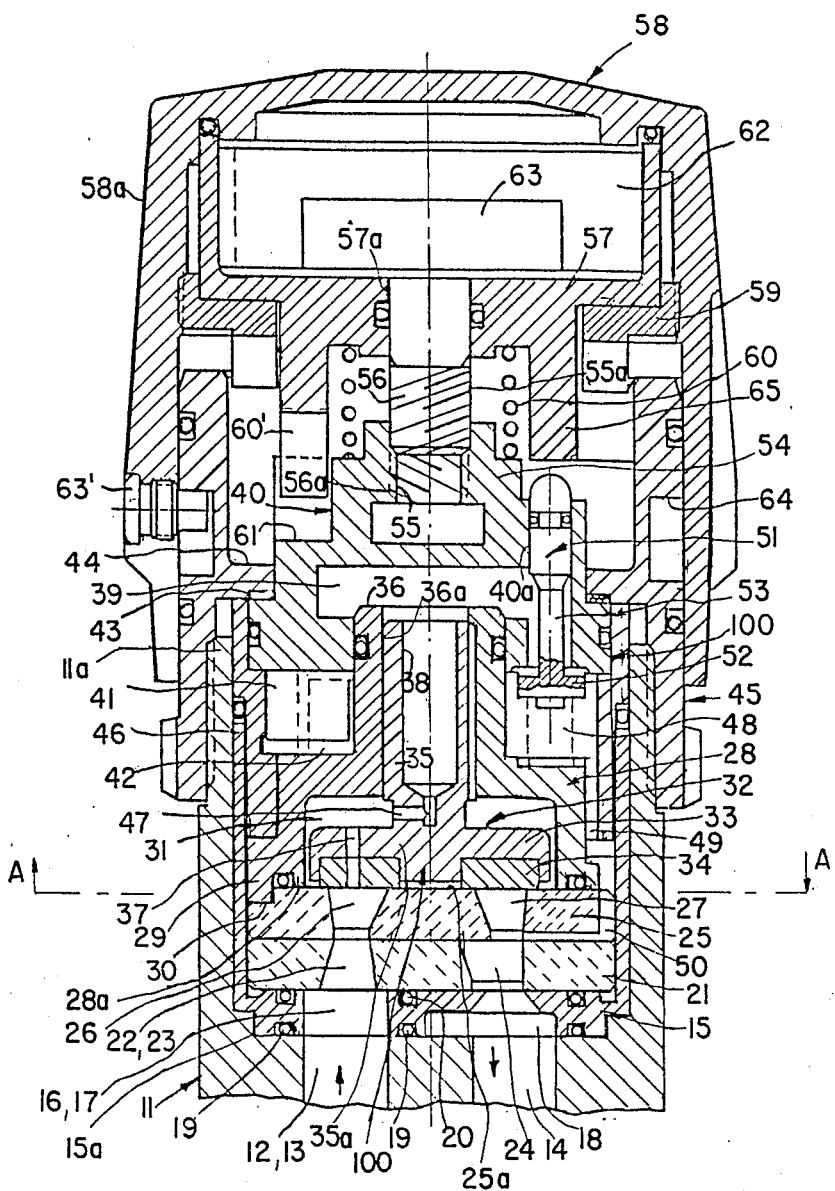
FIG. 1 is a simplified longitudinal sectional view through those components or parts of the mixing device for hot and cold water which are here of interest and needed for understanding the present invention.

Having now had the benefit of the foregoing description of the exemplary embodiment of hot and cold water mixing device or mixing battery, there will now be described the operation thereof which is as follows:

In the illustrated closed position of the fluid mixing device as depicted in FIG. 1 there prevails in the chamber or compartment 39 the same pressure which exists at the inlet-side throughpassage or opening 26. This pressure exerts a sufficient pressure or force upon the entire cross-sectional surface or area of the shaft or shaft member 35 in order to retain the closure portion or element 32 of the servo valve 100 in its closed position. If the valve plate 33 of the servo valve 100 were circumferentially sealed with respect to the inner wall of the chamber 31, something which is absolutely possible, then the closure or closing force would be increased by the pressure which acts upon the annular or ring surface of the valve plate 33 which faces away from the seal 34.

By applying pressure at or depressing the operating or manipulating cap 58 the latter in conjunction with the bowl or dish portion 57 is displaced downwardly in the showing of FIG. 1 against the action of the compression or pressure spring 60. As a result, a projection or extension 65 formed at the bowl or dish portion 57 displaces the plunger or stem member 53 of the pilot valve 51 into its open position. The pressure in the chamber 39 escapes via the channels 49 and 50 to the outlet-side throughpassage or opening 27, so that the closing or closure force acting upon the shaft 35 diminishes. As a result, the valve plate 33 is lifted. Water, the mixing ratio or properties of which depend upon the relative rotational position of the rotary slide 25 in relation to the counter disk 21, thus flows out of the mixed water outlet or outtake 14.

As soon as the pilot valve 51 has again been closed, then an inlet-side pressure again builds-up as a function of the quantity of water flowing through the throttle openings 37 and 47 into the chamber or compartment 39. Due to this build-up of pressure the closure or closing force is again effective at the shaft or shaft member 35.

When the operating cap or cap member 58 is pressed or depressed, then also the threaded pin 56 is pressed into the threaded bore 55, so that the threaded pin 56 rotates. The aforedescribed mechanism 63 can be a suitable timer, such as a commentional clockwork device. This timer mechanism can be wound up by the threaded pin 56 and does not allow the threaded pin 56 throughout a certain period of time to rotate back even when exposed to the action of the compression or pressure spring 60 and then only releases the threaded pin 56 after the expiration of such predeterminate clock time. As a result, it is possible to open the mixing device or battery by operating the operating or manipulating cap 58 one time and to retain such in its open position throughout a time interval which can be predetermined by the aforedescribed mechanism 63 here, for instance, assumed to be a clockwork or timer.

On the other hand, this mechanism 63 also can be constructed as a bistable spring lever mechanism which, after the initial actuation or depression of the operating cap 58, arrests the threaded pin 56 in its turned-in or depressed position and only again releases such threaded pin 56 after there has been accomplished a second actuation or application of pressure to the operating or engagement cap 58.

Furthermore, it is also possible to hydraulically or pneumatically actuate by remote control the pilot valve 51, for instance in that through the application of an additional pressure pulse the pressure in the chamber 39 is increased beyond the prevailing pressure to such an extent that there is overcome the spring or resilient force which is effective at the valve closure portion 52 of the pilot valve 51 in the valve closing direction.

While there are shown and described present preferred embodiments of the invention, it is to be distinctly understood that the invention is not limited thereto, but may be otherwise variously embodied and practiced within the scope of the following claims. Accordingly,

What I claim is:

1. A mixing device for admixing hot and cold water, comprising:
   rotary slide means for controlling in an opposing sense the inflow of hot and cold water;
   means for suppressing the flow of the hot and cold water through the rotary slide means;
   said flow suppressing means comprising a closure portion of servo valve means; and
   said rotary slide means constituting seat means for said closure portion of said servo valve means.

2. The mixing device as defined in claim 1, further including:

an entrainment hood member;

means for coupling for non-relative rotation said rotary slide means with said entrainment hood member;

said entrainment hood member having an internal chamber which is sealed with respect to said rotary slide means;

said closure portion being arranged in said internal chamber;

said rotary slide means comprising an inlet-side throughpassage and an outlet-side throughpassage;

said closure portion being provided with first throttle opening means;

said internal chamber flow communicating by means of said first throttle opening means with said inlet-side throughpassage of the rotary slide means;

means cooperating with said entrainment hood member for defining a further chamber;

said servo valve means being provided with a second throttle opening means;

said internal chamber flow communicating by means of said second throttle opening means with said further chamber;

said servo valve means including pilot valve means;

channel means cooperating with said outlet-side throughpassage of the rotary slide means; and said further chamber being connectable by said pilot valve means of said servo valve means and via said channel means with said outlet-side throughpassage of the rotary slide means.

3. The mixing device as defined in claim 2, wherein:
said closure portion of said servo valve means comprises a membrane; and
said membrane being provided with said first throttle opening means.

4. The mixing device as defined in claim 2, wherein:
said closure portion comprises a valve plate;
a valve shaft member connected with said valve plate;
seal means cooperating with said valve plate; and
said valve shaft member being mounted to be lengthwise displaceable but non-rotatable in said entrainment hood member.

5. The mixing device as defined in claim 4, wherein:
said first throttle opening means is formed in said valve plate;
said valve shaft member comprising a blindhole bore opening into said further chamber; and
said second throttle opening means leading to said blindhole bore.

6. The mixing device as defined in claim 2, wherein:
said pilot valve means comprises a valve closure portion; and
means for pre-biasing said valve closure portion of said pilot valve means into a predetermined closed position.

7. The mixing device as defined in claim 6, wherein:

said pilot valve means comprises a plunger at which there is mounted the valve closure portion of the pilot valve means;

said means cooperating with said entrainment hood member to define said further chamber comprising a coupling sleeve cooperating with said plunger;

said coupling sleeve having a bore in which there is displaceably mounted said plunger; and means for connecting for non-relative rotational movement said coupling sleeve with said entrainment hood member.

8. The mixing device as defined in claim 7, further including:
rotatable and depressible hand grip means;
return spring means coacting with said rotatable and depressible hand grip means;
means for mounting said rotatable and depressible hand grip means to be non-rotatable in relation to said coupling sleeve but axially displaceable against the action of said return spring means; and
rotation of said rotatable and depressible hand grip means enabling rotation of said rotary slide means and depression of said rotatable and depressible hand grip means enabling actuation of said pilot valve means.

9. The mixing device as defined in claim 2, further including:
timer means for delaying return of said pilot valve means into a closed position thereof.

10. The mixing device as defined in claim 8, further including:
timer means for delaying return of said pilot valve means into a closed position thereof; and
said timer means being mounted in said rotatable and depressible hand grip means.

11. The mixing device as defined in claim 8, further including:
stop means for limiting rotation of said rotatable and depressible hand grip means.

12. The mixing device as defined in claim 8, further including:
a bistable spring lever mechanism arranged between said rotatable and depressible hand grip means and the plunger of said pilot valve means so that said pilot valve means can be brought into an open position upon an initial depression of said rotatable and depressible hand grip means and into a closed position upon a further depression of said rotatable and depressible hand grip means.

13. A fluid mixing device for admixing hot and cold fluid, comprising:
displaceable slide means for controlling the flow of hot and cold water;
servo valve means for suppressing the flow of the hot and cold water through the displaceable slide means;
said servo valve means comprising a closure element coacting with said displaceable slide means; and
said displaceable slide means constituting seat means for said closure portion of said servo valve means.

* * * * *